(12) United States Patent
Naot

(10) Patent No.: US 8,379,227 B2
(45) Date of Patent: Feb. 19, 2013

(54) OPTICAL METROLOGY ON TEXTURED SAMPLES

(75) Inventor: Ira Naot, Zichron Yaakov (IL)

(73) Assignee: Nanometrics Incorporated, Milpitas, CA (US)

( * ) Notice: Subject to any disclaimer, the term of this patent is extended or adjusted under 35 U.S.C. 154(b) by 610 days.

(21) Appl. No.: 12/607,970

(22) Filed: Oct. 28, 2009

(65) Prior Publication Data

US 2011/0096339 A1    Apr. 28, 2011

(51) Int. Cl.
*G01B 11/28* (2006.01)
*G01B 11/06* (2006.01)

(52) U.S. Cl. ........................ 356/630; 356/632

(58) Field of Classification Search .... 356/237.1–241.6, 356/242.1–243.8, 426–431, 600–640
See application file for complete search history.

(56) References Cited

U.S. PATENT DOCUMENTS

| | | | |
|---|---|---|---|
| 5,555,474 A * | 9/1996 | Ledger | 356/632 |
| 6,472,238 B1 * | 10/2002 | Wen | 438/16 |
| 7,061,613 B1 | 6/2006 | Huang et al. | |
| 7,151,609 B2 * | 12/2006 | Chalmers et al. | 356/630 |
| 7,324,214 B2 * | 1/2008 | De Groot et al. | 356/511 |
| 7,469,164 B2 * | 12/2008 | Du-Nour | 700/110 |
| 7,840,917 B2 * | 11/2010 | Bae et al. | 716/102 |
| 7,910,822 B1 * | 3/2011 | Funcell | 136/244 |
| 2007/0046953 A1 * | 3/2007 | De Groot et al. | 356/512 |

FOREIGN PATENT DOCUMENTS

EP    1 360 554 B1    2/2006

OTHER PUBLICATIONS

International Search Report and Written Opinion for PCT Application No. PCT/US2010/053182 mailed on Dec. 13, 2010, eight pages.
B. Sopori, Y. Zhang, W Chen, "Process Monitoring in Solar Cell Manufacturing", Conference Paper Presented at 9th Workshop on Crystalline Silicon Solar Cell Materials and Processes, Aug. 1999, p. 1-7.
International Preliminary Report on Patentability mailed on May 10, 2012 for PCT Application No. PCT/US2010/053182 filed Oct. 19, 2010, eight pages.
Hahn, David W., "Light Scattering Theory," Department of Mechanical and Aerospace Engineering, University of Florida, Jul. 2009, thirteen pages.

* cited by examiner

*Primary Examiner* — Gregory J Toatley
*Assistant Examiner* — Jarreas C Underwood
(74) *Attorney, Agent, or Firm* — Silicon Valley Patent Group LLP

(57) ABSTRACT

One or more parameters of a sample that includes a textured substrate and one or more overlying films is determined using, e.g., an optical metrology device to direct light to be incident on the sample and detecting light after the incident light interacts with the sample. The acquired data is normalized using reference data that is produced using a textured reference sample. The normalized data is then fit to simulated data that is associated with a model having an untextured substrate and one or more variable parameters. The value(s) of the one or more variable parameters from the model associated with the simulated data having the best fit is reported as measurement result.

28 Claims, 6 Drawing Sheets

OPTICAL METROLOGY ON TEXTURED SAMPLES

BACKGROUND

Spectral reflectometry is based on acquiring the reflected spectrum from the sample of interest, normalizing it relative to the reflected spectrum of a known reference sample, and then fitting a model to the normalized spectrum. The values of film parameters (thickness of layers, refractive index, etc.) that produce the best fit between the theoretical model and the measured spectrum are reported as the results.

Standard spectral-reflectometry systems and similar optical metrology methods are designed for samples that include films stacked on a polished substrate. Conventionally, the acquired data is normalized using data for a polished reference sample and a model is fit to the normalized spectrum. Where the sample includes a textured substrate, such as used in photovoltaics, a complex theoretical model is required to characterize the effects of the substrate texture on the sample reflectivity. Additionally, the illumination conditions that are used to obtain the data for the polished reference sample are very different from the illumination conditions to measure a textured sample, which further increases the complexity of the metrology.

In high volume solar cell manufacturing, where highly textured substrates are commonly used, the common practice in production monitoring is to periodically insert a "witness" sample, which includes a polished substrate. The witness sample is processed along with the production samples and parameters of the witness sample, such as film thickness, is measured using standard reflectometry, assuming that the measured parameter on the witness sample is correlated to the same parameter on the textured production sample. While standard reflectometry is easier to perform on an untextured witness sample than preparing complex models to characterize the effects of texturing on the sample reflectivity, the correlation to the textured production sample may be poor. In addition, the witness samples introduce an added cost to production for facilitating process monitoring.

Accordingly, improvements for optical metrology of textured samples are desirable.

SUMMARY

One or more parameters of a sample that includes a textured substrate and one or more overlying films is determined using, e.g., an optical metrology device to direct light to be incident on the sample and detecting light after the incident light interacts with the sample. The acquired data is normalized using reference data that is produced using a textured reference sample. The textured reference sample includes a textured substrate, which may be textured using the same texturing process as the sample under test. The normalized data is then fit to simulated data that is associated with a model having an untextured substrate and one or more variable parameters. The simulated data may be stored in a library or calculated in real time. The value(s) of the one or more variable parameters from the model associated with the simulated data having the best fit is reported as measurement result.

DETAILED DESCRIPTION

Figure 1:
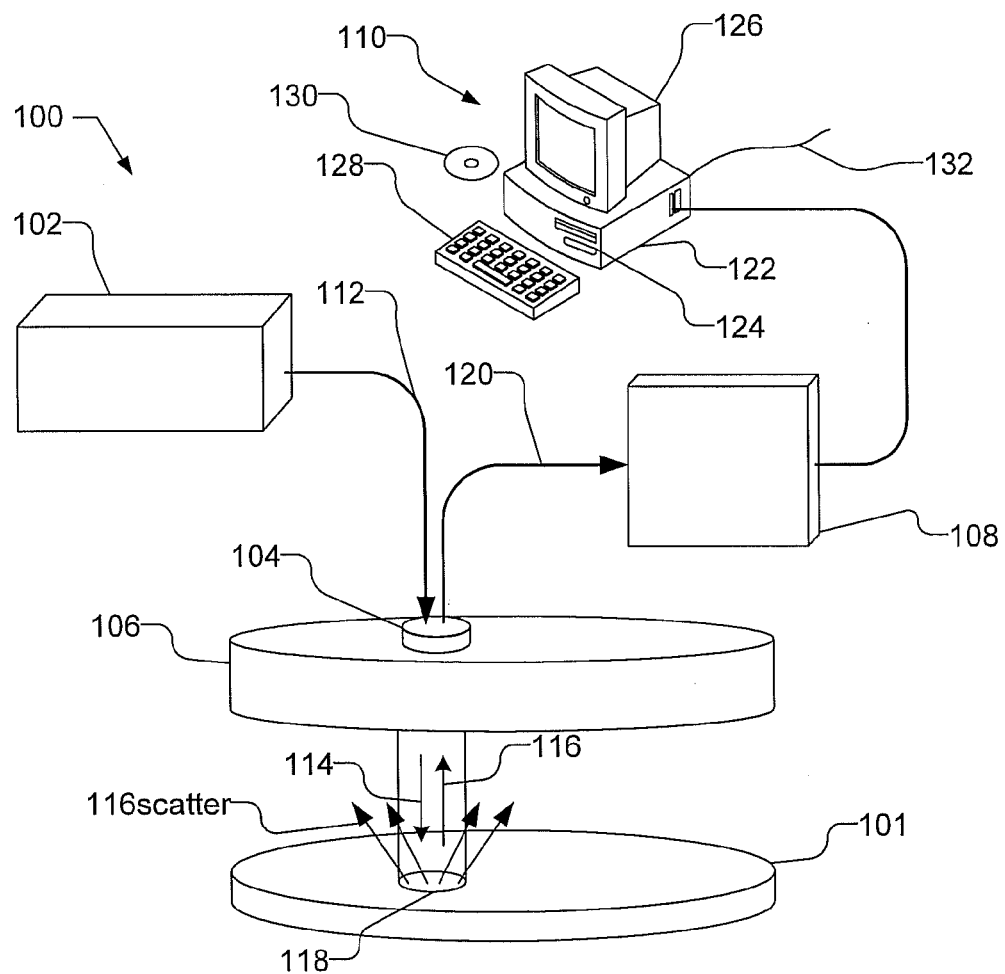
FIG. 1 illustrates a metrology device that may be used to measure the values of film parameters of a textured sample, e.g., a sample that includes one or more films overlying a textured substrate.

FIG. 1 illustrates a metrology device 100 that may be used to measure the values of film parameters on a sample 101 that includes a film overlying a textured substrate. Metrology device 100 may be similar to the metrology device described in U.S. Pat. No. 7,469,164, entitled "Method and Apparatus for Process Control With In-Die Metrology" to Ofer Du-Nour, which is incorporated herein by reference. The metrology device 100 may include a light source 102, an emitter/receiver 104, an emitter/receiver array 106, a spectrometer 108, and computer 110. The light from light source 102 may be coupled to the emitter/receiver 104, e.g., via an optional fiber optic conductor 112. The emitter/receiver 104 is configured to emit an incident light beam 114 at the sample 101 and to receive light returning 116 from the sample 101. The returning light 116 from the emitter/receiver 104 is coupled to the spectrometer 108 via another fiber optic conductor 120. In some embodiments, the emitter/receiver 104 may be optically coupled to the light source 102 and/or the spectrometer 108 without the fiber optic conductors 112, 120.

The light source 102 may produce polychromatic light in the one or more of the visible, infrared, and/or ultraviolet wavelengths. In various embodiments, the light source 102 may include an incandescent light, plasma-discharge, LED or laser. For example, a UV-Visible wavelength range of 200 nm to 1000 nm may be used. Further, wavelengths in the NIR wavelength range, e.g., from 800 to 1700 nm, may also be used. The incident light beam 114 may be polarized or unpolarized light. In various embodiments, the light source 102 may be configured to provide a continuous incident light beam 114, pulsed incident light beam 114, or an on-demand incident light beam 114.

Figure 2A:
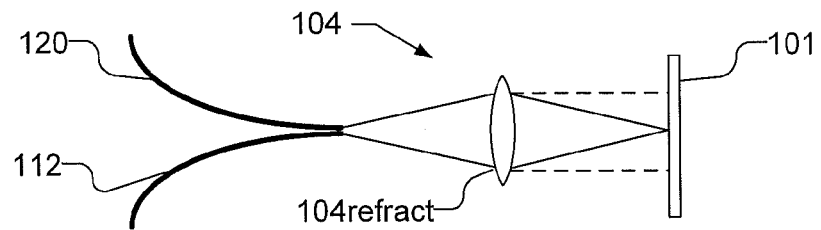
FIGS. 2A, 2B, and 2C illustrate different embodiments of the emitter/receiver.
Figure 2B:
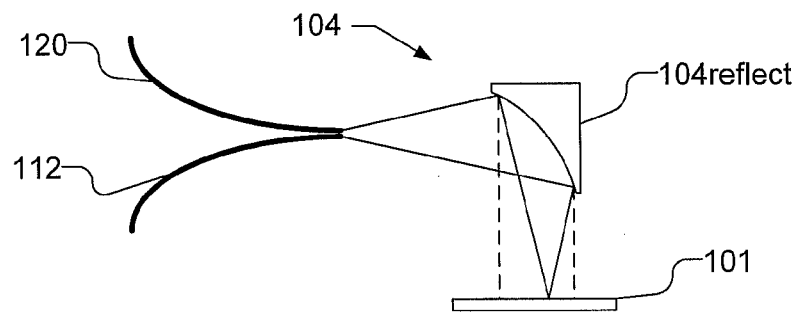
Figure 2C:
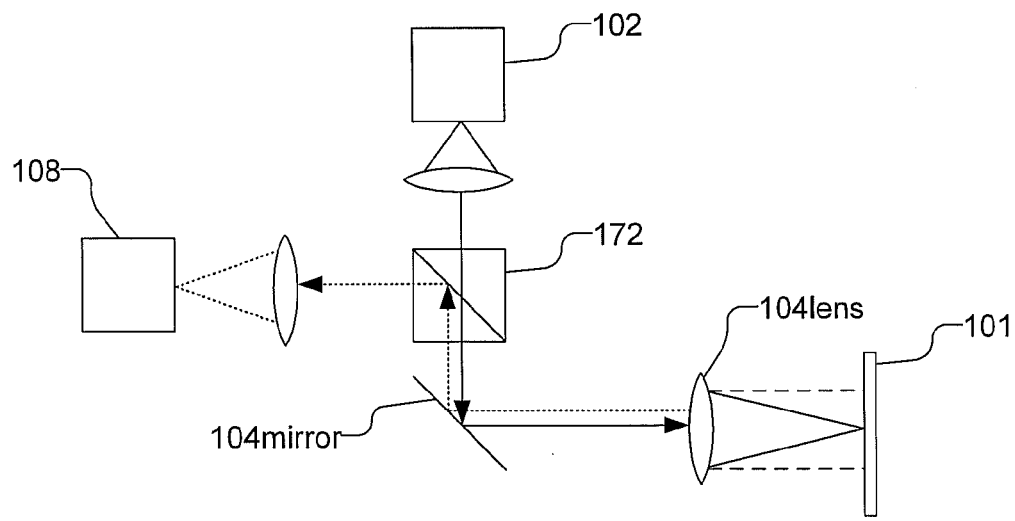

The emitter/receiver 104 is an optical assembly that may include lenses, mirrors and optical fibers, delivering light to the sample and collecting light reflected by the sample. Additionally, the emitter/receiver 104 may include optical components configured to collimate or focus the incident light beam 114, using techniques which are known in the optic art. FIGS. 2A and 2B, for example, illustrate embodiments where the emitter/receiver 104 is optically coupled to fiber optic conductors 112 and 120 and is formed from a refractive lens 104 refract and a reflective lens 104 reflect, respectively, and focuses or collimates (illustrated with broken lines) the light on the sample 101. FIG. 2C is an example of a free-space embodiment in which the emitter/receiver 104 is in a formed of a mirror 104 mirror that is used to steer the light to the sample 101 via lens 104 lens from a beam splitter light 172 that is between light source 102 and spectrometer 108. The emitter/receiver 104 in FIG. 2C may be considered the mirror 104 mirror lens 104 lens and/or beam splitter 172. Other embodiments of the emitter/receiver may be used if desired.

Figure 3:
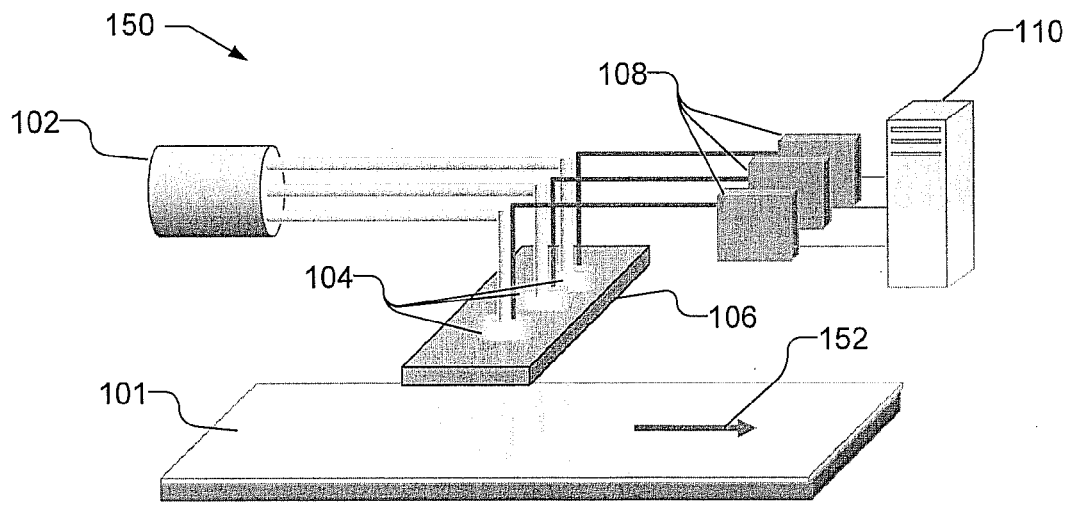
FIG. 3 illustrates another metrology device that may be used to measure the values of film parameters of a textured sample.

The emitter/receiver array 106 is configured to hold the emitter/receiver 104 in a position for emitting the incident light beam 114 at the sample 101. While only one emitter/receiver 104 is illustrated in the emitter/receiver array 106 of FIG. 1, it is contemplated that a plurality of emitter/receivers 104 may be held by the emitter/receiver array 106, as illustrated in FIG. 3. Multiple emitter/receivers 104 disposed in the emitter/receiver array 106 may provide simultaneous measurements at multiple sites on the sample 101, thus enhancing throughput. In some embodiments, the emitter/receiver 104 may be configured to emit the incident light beam 114 normal to the sample 101. In some embodiments, there can be one emitter/receiver 104 that is moved relative to the sample to measure several spots sequentially.

The incident light beam 114 illuminates a region 118 on the sample 101 and is at least partially reflected by the sample 101 becoming returning light 116. In general, it is desirable that the illuminated region 118 be sufficiently larger than the character features in the texturing of the sample, e.g., approximately 10× larger, that the effect that the texturing on the sample 101 has on the incident light 114 is averaged. For example, the illuminated region 118 may be a spot with a diameter of at least 10 mm. However, spot size can range from 0.05 mm (focused) to 30 mm, or larger if desired. As illustrated in FIG. 1, a portion of the incident light is scattered by the sample 101, becoming scattered light $116_{scatter}$, due to the textured substrate of the sample 101. The emitter/receiver 104 receives the returning light 116, but does not receive all of the scattered light $116_{scatter}$. While emitter/receiver 104 is illustrated as emitting and receiving both incident light 114 and returning light 116, the emitter/receiver 104 may be two separate elements, e.g., held at separate locations on the emitter/receiver array 106, one of which emits the incident light 114 and the other receives returning light 116.

The returning light 116 is provided from the emitter/receiver 104 to the spectrometer 108, e.g., by fiber optic conductor 120. The spectrometer 108 receives the returning light 116 and separates the returning light 116 into its constituent wavelengths, the intensity of which is then detected by a detector, such as a CCD array. The spectrometer 108 is coupled to and provides a signal to the computer 110 for the measured intensity as a function of wavelength for the detected light.

The computer 110 is configured to receive the signal from the spectrometer 108. The computer included a processor 122 with memory 124, as well as a user interface including e.g., a display 126 and input devices 128. A computer-usable medium 130 having computer-readable program code embodied may be used by the computer 110 for causing the processor 122 to control the metrology device 100 and to perform the functions including the analysis described herein. The data structures and software code for automatically implementing one or more acts described in this detailed description can be implemented by one of ordinary skill in the art in light of the present disclosure and stored, e.g., on a computer readable storage medium 130, which may be any device or medium that can store code and/or data for use by a computer system such as processor 122. The computer-usable medium 130 may be, but is not limited to, magnetic and optical storage devices such as disk drives, magnetic tape, compact discs, and DVDs (digital versatile discs or digital video discs). A communication port 132 may also be used to receive instructions that are used to program the computer 110 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

FIG. 3 illustrates a metrology device 150 that is similar to metrology device 100, like designated elements being the same. Metrology device 150, however, includes a plurality of emitter/receivers 104 held by the emitter/receiver array 106. With the use of multiple emitter/receivers 104 disposed in the emitter/receiver array 106, simultaneous measurements at multiple sites on the sample 101 may be provided, thereby enhancing throughput. As illustrated by the arrow 151 in FIG. 3, the sample may be moved during measurement.

Figure 4:
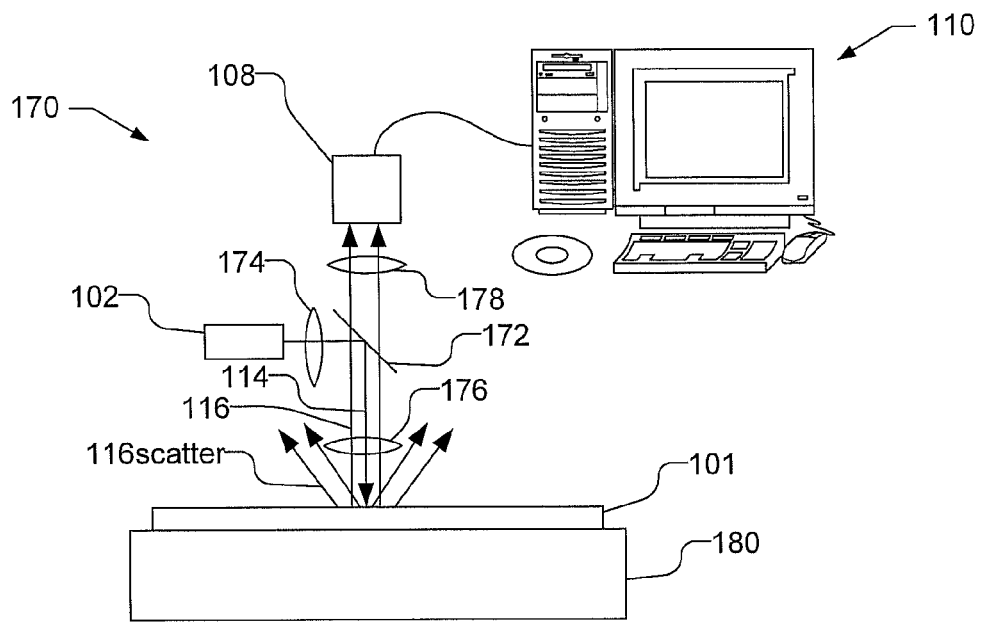
FIG. 4 illustrates yet another metrology device that may be used to measure the values of film parameters of a textured sample.

FIG. 4 illustrates another metrology device 170 that is similar to metrology device 100, like designated elements being the same. Metrology device 170, however, does not use fiber optic conductors 112 and 120. As illustrated in FIG. 4, a beam splitter 172 and optics 174, 176, and 178 are used with light source 102 and spectrometer 108 to emit and to receive incident light 114 and returning light 116, respectively. Additionally, sample 101 is illustrated as being held on a stage 180 in FIG. 4. It should be understood that other configurations of the metrology device may be used to measure a textured sample if desired, including obliquely incident light. For the sake of simplicity, any metrology device capable of measuring a textured sample as described herein, including metrology devices 150, 170, or any other metrology device, will be referred to herein as metrology device 100 unless specifically stated otherwise.

Figure 5A:
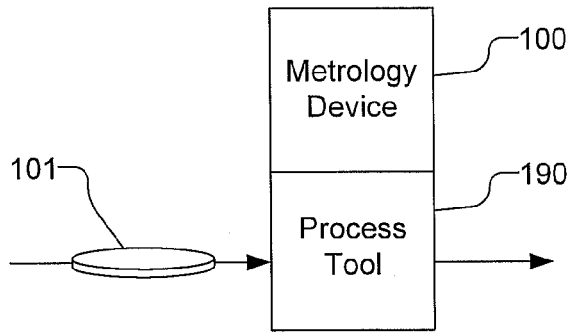
FIGS. 5A and 5B are block diagrams illustrating integrated and stand-alone environments, respectively, for processing and measuring a textured sample.
Figure 5B:
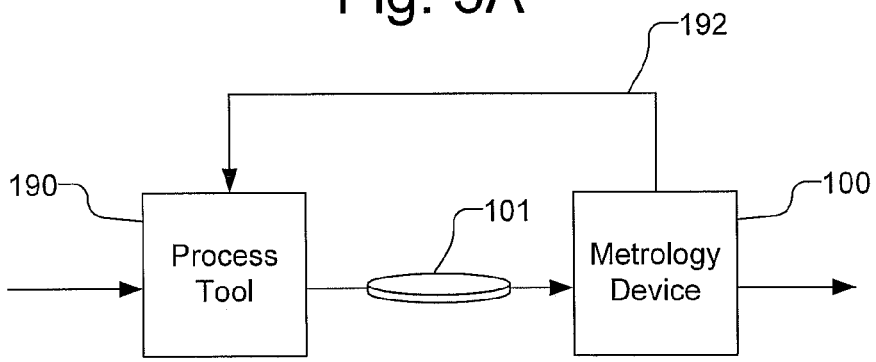

FIGS. 5A and 5B are block diagrams illustrating integrated and stand-alone environments, respectively, for processing and measuring textured sample 101. The metrology device 100 is configured to measure a property of at least one layer of material on the sample 100 that that has been or is being deposited, removed, and/or modified by the process tool 190. As illustrated in FIG. 5A, the metrology device 100 may be configured to be coupled to, i.e., i.e., integrated with, a process tool 190 so that the sample 101 is measured while the sample 101 is located inside a process tool 190. Alternatively, the metrology device 100 may be located separate from the process tool 190, as illustrated in FIG. 5B. A stand alone metrology device 100, such as that shown in FIG. 5B may be configured to illuminate the sample 101 as the sample is moved from one location to another, e.g., as illustrated in FIG. 3 by the sample 101 moving as illustrated by arrow 152. Alternatively, the sample 101 may be loaded on a stage in metrology device 100 and be measured while the sample 101 is in the metrology device 100, as illustrated by stage 180 in FIG. 4. In either configuration, the metrology device 100 may be provide information about the measurement of sample 101 to the process tool 190, e.g., in a feedback or feed forward loop illustrated by loop 192 in FIG. 5B, to control the processing of the sample 101 or subsequently processed samples.

Figure 6:
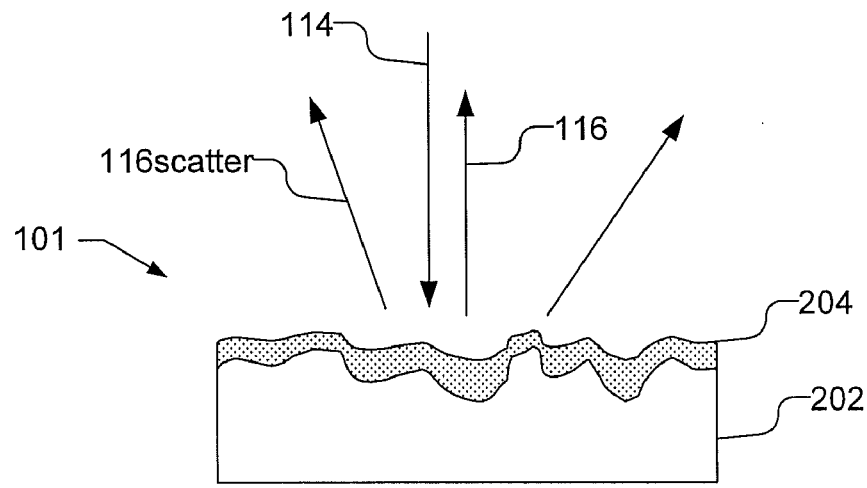
FIG. 6 illustrates a cross-sectional view of a portion of a textured sample, which includes a textured substrate with an overlying film.

FIG. 6 illustrates a cross-sectional view of a portion of a sample 101 that includes a textured substrate 202 with an overlying film 204. While a single film 204 is illustrated in FIG. 6, it should be understood that multiple films may be present. Textured substrates are used, e.g., in the photovoltaic industry, but the present invention may be used with any sample with a textured substrate regardless of specific industry. The substrate 202 may be, e.g., poly-silicon, that is textured by etching or that is textured by producing one or more textured films on the substrate 202 used in photovoltaic cell manufacturing, such as CIGS, Cadmium Telluride, or textured single-crystal silicon. As used herein, a textured substrate includes a substrate that is textured itself or a substrate with a textured film overlying the substrate, where the transparent or partly transparent films deposited on the textured substrate (e.g., including any textured films) can be measured in the method described herein. Texture characteristic size may be from 0.05 microns to 20-30 microns. The overlying film 204 may be silicon-oxide, silicon nitride, metal-oxide films such as ZnO, SnO, ITO, CdS or any other transparent or semi-transparent film. Deposition methods of the overlying film 204 typically include thermal oxidation, chemical vapor deposition, physical vapor deposition (AKA PVD or "Sputtering") liquid-solution coating, ink-jet printing or other thin-film deposition or formation methods. As illustrated in FIG. 6, a portion of the incident light 114 is reflected as returning light 116, and the remainder of the incident light 114 is scattered $116_{scatter}$ due to the textured substrate 202. Typically for a textured sample 101 used for, e.g., a solar cell, the characteristic size of the texture of substrate 202 is much larger than the wavelength of light used by metrology device 100 and the thickness of the film 204 is much smaller than the texture size. Consequently, the light scattering is due to angles of the surfaces of the textured substrate 202 and may be considered wavelength independent. Further, there is little effect from multiple reflections between neighboring surfaces in the textured substrate 202 and the non-uniform optical path inside the film of interest, e.g., film 204.

Figure 7:
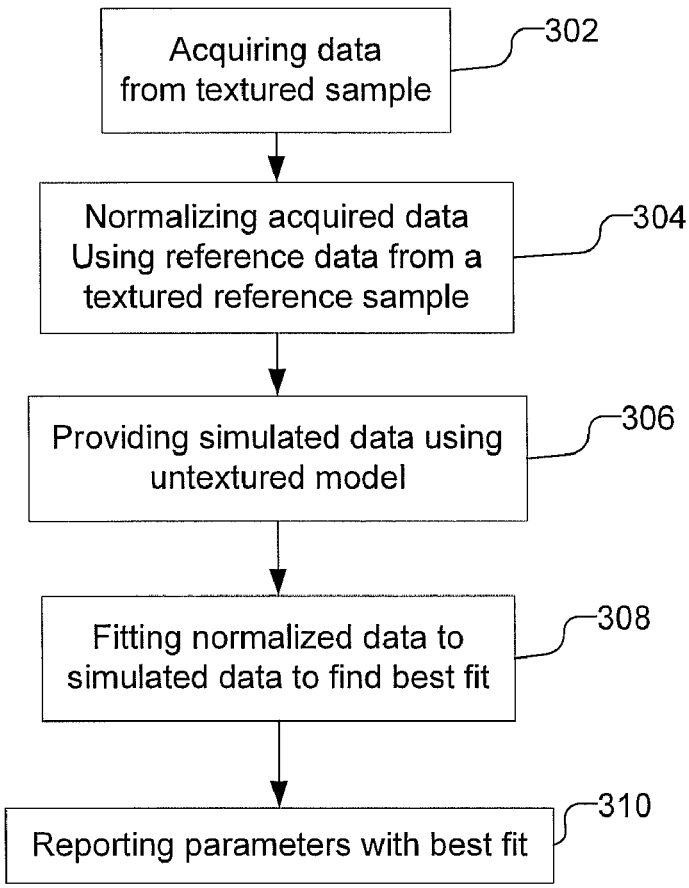
FIG. 7 is a flow chart illustrating a method of measuring textured sample.

FIG. 7 is a flow chart illustrating a method of measuring textured sample, and in particular, measuring one or more parameters of a film on a sample having a textured substrate. The textured sample that is under test may be, e.g., a photovoltaic wafer or panel. As illustrated in FIG. 7, data is acquired from the textured sample (302), e.g., using metrology device 100. The data may be, e.g., spectral information of the returning light 116, detected by spectrometer 108. The acquired data is transformed into values for one or more physical parameters of the sample as follows.

Figure 8:
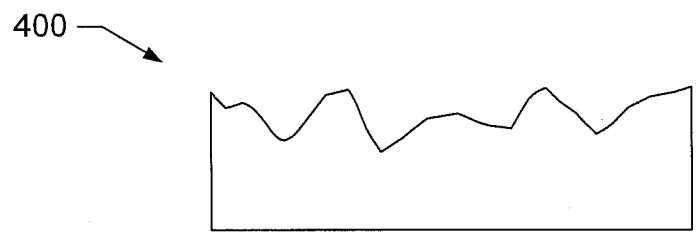
FIG. 8 illustrates a cross-sectional view of a portion of a textured reference sample.
Figure 10:
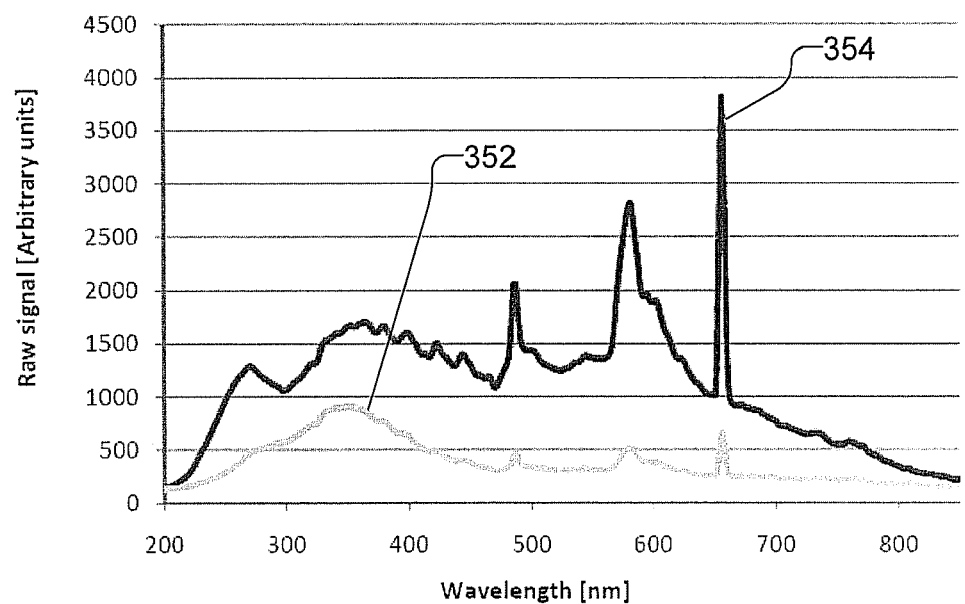
FIG. 10 illustrates raw signal spectra for a textured sample under test and a textured reference sample.
Figure 11:
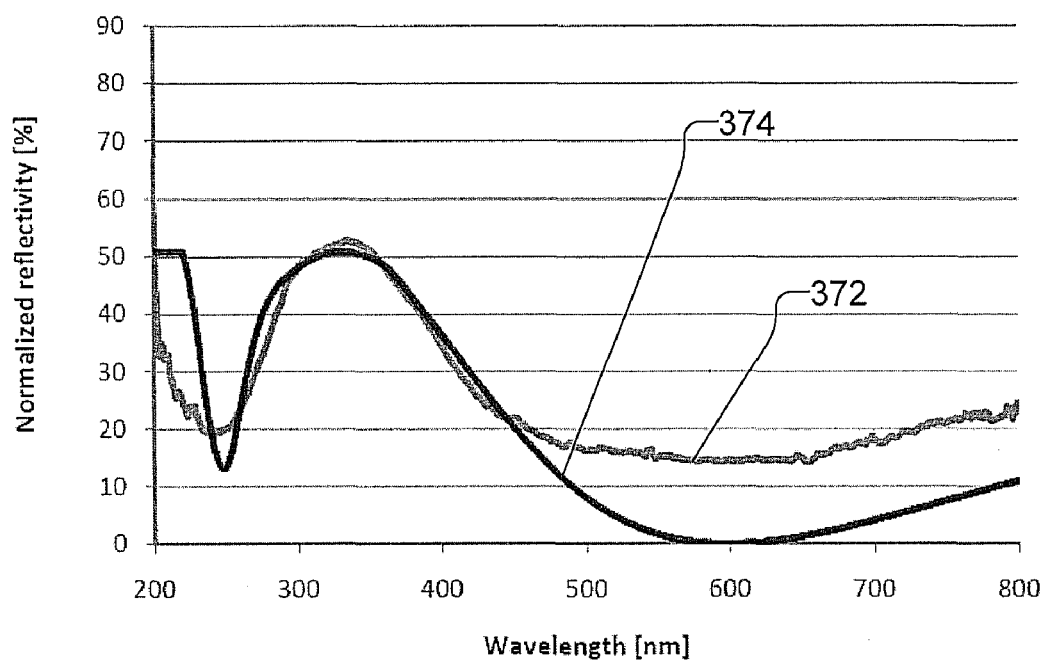
FIG. 11 illustrates normalized reflectivity spectra for normalized spectra and simulated spectra.

The acquired data is normalized using reference data from a textured reference sample (304). FIG. 8 illustrates a cross-sectional view of a portion of a textured reference sample 400. The textured reference sample 400 is, e.g., a reference substrate that is textured in the same manner as the sample 101 under test. The textured reference sample 400 may be textured differently than the sample under test, but the accuracy of the calibration will be decreased. The textured reference sample 400 may be a bare silicon substrate that is textured using the same texturing process as the sample under test. The textured reference sample 400 is measured by the same metrology device as used to measure the sample under test in order to provide the reference data that is used to normalize the data acquired from the textured sample under test. Because illuminated region 118 on both the sample under test and the textured reference sample 400 is large relative to the size of the texturing, the effect that the texturing has on the incident light 114 is averaged. The reference data may be stored, e.g., in memory 124 of the computer 110. The reference data from the textured reference sample 304 is then used to normalize the acquired data from the sample under test. The raw spectrum collected by the spectrometer includes effects of the light source spectrum, acquisition conditions, effect of the system optics and the reflectivity of the sample of interest. Normalizing means a mathematical manipulation by which the raw spectrum is compared to the spectrum from a reference sample acquired in similar conditions so all effects of the light source, system, and acquisition conditions can be compensated for and the normalized spectrum contains information on the reflectivity of the sample of interest (absolute or relative to some reference standard). By way of example, FIG. 10 illustrates a raw signal spectra 350, in arbitrary units from a textured sample and spectra 352 from a textured reference sample, as a function of wavelength. FIG. 11 illustrates the normalized reflectivity (%) of the normalized data as spectra 372.

Figure 9:
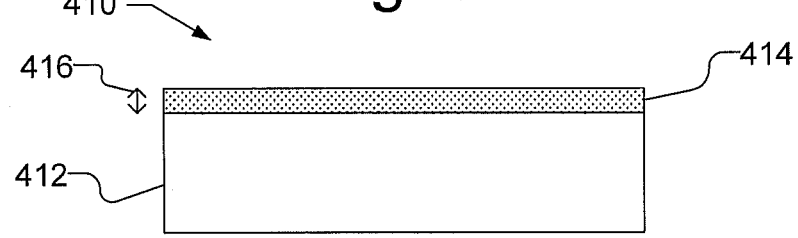
FIG. 9 illustrates an untextured model of a textured sample under test, the untextured model including an untextured substrate and the overlying film and one or more variable parameters.

The sample under test is modeled using an untextured model, which is a model of the sample that includes one or more variable parameters and an untextured substrate. FIG. 9 illustrates an untextured model 410 of the sample under test, which includes the untextured substrate 412 and the overlying film 414 and includes one or more variable parameters, illustrated as the thickness of film 414 by arrow 416. As illustrated in FIG. 9, the untextured substrate 412 is modeled as being smooth, rather than as textured shown in FIG. 6. The one or more variable parameter in the model 410 is the parameter or parameters being measured. Of course, if the sample under test includes multiple films, the model 410 will include the multiple films and may include variable parameters of one or more of the films, such as thicknesses, and/or refractive index. Various material properties, such as composition, impurity content, degree of crystallinity (or variations in properties) can then be correlated to the variations of the refractive index. Simulated data, e.g., a simulated spectrum, is calculated based on the model 410 based on known principles of physical optics, such as Fresnel's equations or other calculation methods such as frequency analysis of the signal, and are dependent on the thickness and optical constants of the layers. FIG. 11 illustrates a simulated data as spectrum 374. The simulated data may be stored in, e.g., memory 124 of computer 110.

The normalized data is fit to the modeled data to find a best fit (308). The best fit may be determined using, e.g., Mean Squared Error (MSE), which quantifies the difference between the data, where the best fit is defined as the minimum MSE or when the MSE is below a predetermined threshold. The best fit may be found through regression analysis, such as a non-linear regression, where the unknown parameter of the model, e.g., thickness, is varied until best fit occurs. The varying of the unknown parameter and calculation of the associated simulated data may be performed in real time, or alternatively, may be pre-calculated and stored in a library that is stored in, e.g., memory 124 of computer 110.

Once a best fit is found, the parameters in the model are presumed to accurately describe parameter the sample under test and are thus reported as the result (310), e.g., by storing the parameters in memory 124 of computer 110, by displaying on display 126 or otherwise recording the results.

The use of the textured reference sample to normalize the measured data permits the use of an untextured model to calculate the simulated data, which greatly simplifies the modeling of the sample compared to conventional metrology techniques which attempt to accurately characterize the textured substrate during modeling.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of determining one or more parameters of a sample having a textured substrate and one or more overlying films, the method comprising:
   acquiring data from the sample having a textured substrate and one or more overlying films by using an optical metrology device to direct light to be incident on the sample and detecting light after the incident light interacts with the sample;
   providing the acquired data to a computer;
   normalizing the acquired data with the computer using reference data from a textured reference sample;
   fitting the normalized data to simulated data with the computer to find simulated data with a best fit, the simulated data being associated with a model having an untextured substrate and one or more variable parameters; and
   reporting values of the one or more variable parameters of the model that corresponds to the simulated data with the best fit.

2. The method of claim 1, wherein the light that is incident on the sample forms a spot on the sample that is 50 microns to 30 millimeters in diameter.

3. The method of claim 1, further comprising acquiring the reference data from the textured reference sample by using the optical metrology device to direct light to be incident on the textured reference sample and detecting light after the incident light interacts with the textured reference sample.

4. The method of claim 1, wherein the textured reference sample comprises a reference substrate, the reference substrate is textured using the same texturing process as used with the textured substrate of the sample.

5. The method of claim 1, wherein the acquired data and reference data are spectral data.

6. The method of claim 1, wherein the one or more variable parameters comprises the thickness of one or more overlying films.

7. The method of claim 1, wherein the sample is a photovoltaic wafer or panel.

8. An apparatus for determining parameters of a sample having a textured substrate and one or more overlying films, the apparatus comprising:
   a light source that produces light;
   optics that cause the light to be incident on the sample;
   a detector for detecting light after it interacts with the sample, the detector providing test data in response to the detected light;
   a computer connected to receive the test data from the detector;
   memory connected to the computer, wherein the memory stores reference data from a reference sample that has a textured substrate and the memory stores a simulated data associated with a model with an untextured substrate and one or more variable parameters; and
   software held in the memory and run in the computer to cause the computer to normalize the test data using the reference data, to fit the normalized data to the simulated data to find simulated data with a best fit and to report the values of the one or more variable parameters of the model that corresponds to the simulated data with the best fit.

9. The apparatus of claim 8, further comprising a sample stage for holding the sample having a textured substrate and one or more overlying films.

10. The apparatus of claim 8, wherein the light source, optics and detector are adapted to be coupled to a processing tool, wherein the light source produces light and the optics cause the light to be incident on the sample while the sample is in the processing tool.

11. The apparatus of claim 8, wherein the optics produces a spot of light on the sample that is at least 50 microns in diameter.

12. The apparatus of claim 8, wherein the reference data from the reference sample is produced using the light source and optics to cause the light to be incident on the reference sample and the detector for detecting light after it interacts with the reference sample, the detector providing the reference data to the computer.

13. The apparatus of claim 8, wherein the textured substrate of the reference sample is textured using the same texturing process as used with the textured substrate of the sample.

14. The apparatus of claim 8, wherein the acquired data and reference data are spectral data.

15. The apparatus of claim 8, wherein the one or more variable parameters comprises the thickness of one or more overlying films.

16. The apparatus of claim 8, wherein the sample is a photovoltaic wafer or panel.

17. The apparatus of claim 8, further comprising a library stored in memory, the library including a plurality of models with untextured substrates and one or more variable parameters and simulated data associated with the models.

18. The apparatus of claim 8, wherein the software held in memory and run in the computer further causes the computer to produce a model with an untextured substrate and one or more variable parameters and to calculate the associated simulated data in real time.

19. A computer-readable medium including program code stored thereon, comprising:
   program code to normalize the data acquired from a sample having a textured substrate with one or more overlying films using reference data from a reference sample having a textured substrate;
   program code to fit the normalized data to simulated data from a model that includes an untextured substrate and one or more variable parameters; and
   program code to report values of the one or more variable parameters of the model that is associated with the simulated data with the best fit.

20. A method of determining the values of one or more physical parameters of a sample having a textured substrate and one or more overlying films, the method comprising:
   acquiring data from the sample having a textured substrate and one or more overlying films using an optical metrology device to direct light to be incident on the sample and detecting light after the incident light interacts with the sample;
   providing reference data from a textured reference sample;
   providing simulated data associated with a model including an untextured substrate with one or more variable parameters;
   transforming the acquired data into values of one or more physical parameters of the sample and storing the values of the physical parameters of the sample, wherein transforming the acquired data into values of physical parameters of the sample comprises:
   normalizing the acquired data using the reference data;

fitting the normalized data to the simulated data to find simulated data with a best fit; and reporting the values of the one or more variable parameters of the model that corresponds to the simulated data with the best fit as the values of the physical parameters of the sample.

21. The method of claim 20, wherein the light that is incident on the sample forms a spot on the sample that is at least 50 microns in diameter.

22. The method of claim 20, further comprising acquiring the reference data from the textured reference sample using the optical metrology device to direct light to be incident on the textured reference sample and detecting light after the incident light interacts with the textured reference sample.

23. The method of claim 20, wherein the textured reference sample comprises a reference substrate, the reference substrate is textured using the same texturing process as used with the textured substrate of the sample.

24. The method of claim 20, wherein the acquired data and reference data are spectral data.

25. The method of claim 20, wherein the one or more variable parameters comprises the thickness of one or more overlying films.

26. The method of claim 20, wherein the sample is a photovoltaic wafer.

27. The method of claim 20, wherein providing simulated data associated with a model including an untextured substrate with one or more variable parameters comprises providing a library including a plurality of models with untextured substrates and one or more variable parameters and simulated data associated with the models.

28. The method of claim 20, wherein providing simulated data associated with a model including an untextured substrate with one or more variable parameters comprises producing a model with an untextured substrate and one or more variable parameters and calculating the associated simulated data in real time.

* * * * *